(12) United States Patent
Akiyama et al.

(10) Patent No.: US 8,216,147 B2
(45) Date of Patent: Jul. 10, 2012

(54) ULTRASONOGRAPHIC EQUIPMENT

(75) Inventors: Hisashi Akiyama, Kanagawa (JP); Kiyoshi Fujii, Kanagawa (JP); Keiji Shintani, Tokyo (JP); Satoru Uchikawa, Tokyo (JP); Makoto Kondo, Kanagawa (JP)

(73) Assignee: Panasonic Corporation, Osaka (JP)

( * ) Notice: Subject to any disclaimer, the term of this patent is extended or adjusted under 35 U.S.C. 154(b) by 1008 days.

(21) Appl. No.: 10/599,594

(22) PCT Filed: Apr. 8, 2005

(86) PCT No.: PCT/JP2005/006941
§ 371 (c)(1),
(2), (4) Date: Jan. 4, 2007

(87) PCT Pub. No.: WO2005/096948
PCT Pub. Date: Oct. 20, 2005

(65) Prior Publication Data
US 2007/0272021 A1  Nov. 29, 2007

(30) Foreign Application Priority Data
Apr. 8, 2004 (JP) .................... 2004-114713

(51) Int. Cl.
*A61B 8/00* (2006.01)
(52) U.S. Cl. ............. 600/444; 600/437; 600/443
(58) Field of Classification Search .............. None
See application file for complete search history.

(56) References Cited

U.S. PATENT DOCUMENTS

| 5,152,294 | A | * | 10/1992 | Mochizuki et al. | 600/459 |
| 6,322,506 | B1 | | 11/2001 | Nagai et al. | |
| 6,645,151 | B2 | * | 11/2003 | Irioka et al. | 600/459 |
| 6,780,153 | B2 | * | 8/2004 | Angelsen et al. | 600/444 |
| 7,285,094 | B2 | * | 10/2007 | Nohara et al. | 600/447 |
| 7,457,654 | B2 | * | 11/2008 | Raitzer et al. | 600/407 |

FOREIGN PATENT DOCUMENTS

| JP | 3-184532 | | 8/1991 |
| JP | 08-068639 | A | 3/1996 |
| JP | 2000-23974 | | 1/2000 |
| JP | 2001-70301 | | 3/2001 |
| JP | 2002-78710 | | 3/2002 |
| JP | 2002078710 | A * | 3/2002 |
| JP | 2003-305045 | A | 10/2003 |
| JP | 2002-360566 | | 12/2006 |

* cited by examiner

*Primary Examiner* — Long V. Le
*Assistant Examiner* — Angela M Hoffa
(74) *Attorney, Agent, or Firm* — Pearne & Gordon LLP

(57) ABSTRACT

A technology for structuring a three-dimensional image in a more accurate position spatially even when an ultrasonic transducer unit does not perform oscillation scanning at completely constant angular velocity is disclosed. According to the technology, an oscillation angle detection means 104 detects an oscillation angle of an ultrasonic transducer unit 1, and a three-dimensional image processing means 11 forms a three-dimensional image based on the oscillation angle detected by the oscillation angle detection means and image data outputted from an ultrasonic receiving means 4.

5 Claims, 13 Drawing Sheets

| 1 | 2 | 3 | ... | ... | n-1 | n |
|---|---|---|---|---|---|---|
| ANGLE OF ACOUSTIC LINE 1 | ANGLE OF ACOUSTIC LINE 2 | ANGLE OF ACOUSTIC LINE 3 | ... | ... | ANGLE OF ACOUSTIC LINE n-1 | ANGLE OF ACOUSTIC LINE n |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |
| RECEIVING DATA | RECEIVING DATA | RECEIVING DATA | ... | ... | RECEIVING DATA | RECEIVING DATA |

ULTRASONOGRAPHIC EQUIPMENT

TECHNICAL FIELD

The present invention relates to an ultrasonographic equipment for three-dimensionally acquiring intravital echo data, converting the echo data to image data from a virtual view point, and displaying the image data.

BACKGROUND ART

In general, in an ultrasonographic equipment intended to three-dimensionally display an intravital tissue aspect, the following structure has been known (for example, refer to Japanese Patent Document 1 as below). In the structure, as an ultrasonic probe for capturing three-dimensional echo data, an ultrasonic transducer unit for scanning an ultrasonic beam performs mechanical oscillation scanning in the direction crossing the beam scanning direction. FIG. 12 is an explanation drawing showing a scanning state thereof. In FIG. 12, an ultrasonic transducer unit 1 in an unshown probe includes a plurality of ultrasonic transducer elements which are arranged to align in the horizontal direction X in relation to the surface of a test body (convex in FIG. 12). The ultrasonic transducer unit 1 transmits and receives ultrasonic waves in the depth direction Y of the test body and two-dimensionally scans the X-Y plane. In addition, the ultrasonic transducer unit 1 is oscillated in the direction Z orthogonal to the X-Y plane and scans the oscillation direction Z.

In the foregoing ultrasonic probe, ultrasonic beam scanning (hereinafter referred to as main cross section scanning) and oscillation scanning are concurrently performed. Thereby, it becomes possible to acquire echo data from intravital tissues corresponding to a cross line of the both scanned faces which move every second, that is, acquire three-dimensional echo data. The acquired three-dimensional echo data is provided with processing of structuring a three-dimensional image, that is, processing of converting the three-dimensional echo data to image data from a virtual view point. Then, the image data is displayed by a display method to show the image in the plane as if the image is three-dimensional. Otherwise, a given cross section is displayed.

In structuring a three-dimensional image, it is necessary that direction components in the three-dimensional space of each echo data are known. In such an ultrasonographic equipment using the ultrasonic probe which performs mechanical oscillation scanning, the ultrasonic transducer unit is controlled to be oscillated so that an ideal oscillation angular velocity W in relation to time of the ultrasonic transducer unit results in profile 21 as shown in FIG. 13A, that is, so that an ideal oscillation angle θ in relation to time of the ultrasonic transducer unit results in profile 22 as shown in FIG. 13B. Further, as echo data used for structuring the three-dimensional image, the echo data obtained during period from t1 to t2 when the oscillation angular velocity W is relatively constant (W=w1). Furthermore, the three-dimensional image is structured on the assumption that by performing main cross section scanning at regular time intervals, the main cross section scanned face is a plane and each main cross section is conformal.

In general, for the purpose of improving a three-dimensional echo data acquisition rate per unit time, oscillation is controlled so that the following formula is established.

$$w2 = (-1) * w1$$

On that basis, echo data is acquired during outward and homeward oscillation periods of outward period from t1 to t2 when W is w1 and homeward period t4 to t5 when W is w2. Here, as shown in FIG. 14, when a main cross section scanned face 51 indicated in full line is formed by setting a main cross section scanning direction 53 in an oscillation scanning outward route 56 and the same main cross section scanning direction 53 is used in an oscillation scanning homeward route 55, a main cross section scanned face 52 as indicated in dotted line is created in the oscillation homeward route, that is, discrepancy of scanned face angles is generated between the oscillation outward route and the oscillation homeward route. Therefore, the following method has been proposed (for example, refer to Patent document 2 as below). In the method, a main cross section scanning direction 54 which is the direction opposite to the direction 53 of the outward route is set in the oscillation homeward route. Thereby, discrepancy of scanned face angles between the oscillation outward route and the oscillation homeward route is modified.

Patent document 1: Japanese Patent Application Publication No. 3-184532 (FIG. 2)
Patent document 2: Japanese Patent Application Publication No. 2001-70301 (FIG. 3)

In recent years, a three-dimensional image by an ultrasonographic equipment is used not only for observing an intravital tissue aspect, but also for puncturing a test body while monitoring the three-dimensional image and a guideline, or for measuring a distance, an angle, an area, a volume and the like of organs, tumors, fetuses and the like. Thus, usability thereof has been increased. To meet such medical needs, it is essential that three-dimensional images provided by ultrasonographic equipment are structured more precisely, that is, are structured in a spatially accurate position than ever before.

However, in the foregoing existing ultrasonographic equipment, the three-dimensional image is structured on the assumption that the main cross section scanned face used for structuring the three-dimensional image is a plane, on the presupposition that the ultrasonic transducer unit performs oscillation scanning at constant angular velocity during the period of acquiring the three-dimensional echo data. In general, in mechanical oscillation scanning using a motor, so-called feedback control is used. In the feedback control, a motor impressed voltage or a current in next time is determined by a current oscillation scanning angle or a current oscillation scanning angular velocity, or the both thereof. However, even when the feedback control is performed highly precisely, it is not possible to perform oscillation scanning at a completely constant angular velocity. That is, it is not the fact that a main cross section scanned face of actually acquired echo data is not formed of a complete plane. Each main cross section is formed of a curved face to some extent. In result, in the three-dimensional image structured on the assumption that each main cross section scanned face is a plane, there are problems that the three-dimensional image is distorted or misaligned according to the degree of the curved face, or the image is swung according to oscillation reciprocation. In result, there is the possibility that puncture is performed in the direction shifted from the direction expected by an operator, or measurement errors in a distance, an angle, an area, a volume and the like are large.

DISCLOSURE OF THE INVENTION

In order to solve the above existing problems, it is an object of the invention to provide an ultrasonographic equipment capable of structuring a three-dimensional image in a more accurate position spatially even when an ultrasonic transducer unit does not perform oscillation scanning at completely constant angular velocity.

It is another object of the invention to provide an ultrasonographic equipment capable of creating a three-dimensional image with higher geometric precision in the oscillation direction of an ultrasonic transducer unit when the three-dimensional image is created from two-dimensional images by oscillating the ultrasonic transducer unit.

To attain the foregoing objects, the invention provides an ultrasonographic equipment including an ultrasonic transducer unit in which ultrasonic transducer elements for scanning ultrasonic beam are arranged in a state of an array, a transducer unit oscillating motor for making the ultrasonic transducer unit perform oscillation scanning in the direction crossing the scanning direction of the ultrasonic beam, an oscillation angle detection means for detecting an oscillation angle of the ultrasonic transducer unit, an ultrasonic transmission means for exciting the ultrasonic transducer element to form the ultrasonic beam, an ultrasonic receiving means for forming ultrasonic beam from ultrasonic echo received by the ultrasonic transducer element and converting the ultrasonic beam to visible image data, a three-dimensional image processing means for forming a three-dimensional image based on the oscillation angle detected by the oscillation angle detection means and image data outputted from the ultrasonic receiving means, and an image display means for displaying the three-dimensional image.

By the foregoing structure, even if the ultrasonic transducer unit does not perform oscillation scanning at completely constant angular velocity, an actual oscillation scanning angle corresponding to each acquired ultrasonic echo can be given to the three-dimensional image processing means. Thus, a three-dimensional image can be structured in a more accurate position spatially.

Further, the invention provides an ultrasonographic equipment including an ultrasonic transducer unit in which ultrasonic transducer elements for scanning ultrasonic beam in a state of an array, a transducer unit oscillating motor for making the ultrasonic transducer unit perform oscillation scanning in the direction crossing the scanning direction of the ultrasonic beam, an oscillation angle detection means for detecting an oscillation angle of the ultrasonic transducer unit, an ultrasonic transmission means for exciting the ultrasonic transducer element to form the ultrasonic beam, an ultrasonic receiving means for forming ultrasonic beam from ultrasonic echo received by the ultrasonic transducer element and converting the ultrasonic beam to visible image data, an oscillation angle information adding means for adding information of the oscillation angle detected by the oscillation angle detection means to image data outputted from the ultrasonic receiving means, a three-dimensional image processing means for forming a three-dimensional image based on image data and the added oscillation angle information outputted from the oscillation angle information adding means, and an image display means for displaying the three-dimensional image.

By the foregoing structure, even if the ultrasonic body does not perform oscillation scanning at completely constant angular velocity, an actual oscillation scanning angle corresponding to each acquired ultrasonic echo can be given to the three-dimensional image processing means. Thus, a three-dimensional image can be structured in a more accurate position spatially.

Further, in the ultrasonographic equipment of the invention, the three-dimensional image processing means forms a three-dimensional image based on angle information obtained by smoothing the information of the oscillation angle detected by the oscillation angle detection means.

By the foregoing structure, three-dimensional image processing can be performed based on oscillation angle information equal to or more than the resolution of the minimum oscillation angle obtained by the oscillation angle detection means.

Further, the invention provides an ultrasonographic equipment including an ultrasonic transducer unit which two-dimensionally scans a fault plane of a test body, and is driven to be oscillated in the direction orthogonal to a scanned face of the two-dimensional scanning, a scanning conversion means for recording a receiving signal obtained by the two-dimensional scanning by the ultrasonic transducer unit in a frame memory to create two-dimensional image data, reading out the two-dimensional image data, and outputting the two-dimensional image data, a delay means for delaying position information in the oscillation direction of the ultrasonic transducer unit by processing time of the scanning conversion means, and a three-dimensional image processing means for creating a three-dimensional image from the two-dimensional image data of a plurality of frames sequentially outputted from the scanning conversion means based on the position information in the oscillation direction delayed by the delay means.

By the foregoing structure, input timing of the two-dimensional image data of the plurality of frames inputted to the three-dimensional image processing means and position information in the oscillation direction of the ultrasonic transducer unit are synchronized. Therefore, a three-dimensional image with higher geometrical precision in the oscillation direction of the ultrasonic transducer unit can be created.

Further, the invention provides an ultrasonographic equipment including an ultrasonic transducer unit which two-dimensionally scans a fault plane of a test body, and is driven to be oscillated in the direction orthogonal to a scanned face of the two-dimensional scanning, a scanning conversion means for recording a receiving signal obtained by the two-dimensional scanning by the ultrasonic transducer unit in a frame memory to create two-dimensional image data, writing position information in the oscillation direction of the ultrasonic transducer unit in the frame memory, reading out the two-dimensional image data and the position information, and outputting the two-dimensional image data and the position information, and a three-dimensional image processing means for creating a three-dimensional image from the two-dimensional image data of a plurality of frames and the position information in the oscillation direction which are sequentially outputted from the scanning conversion means.

By the foregoing structure, a three-dimensional image is created from the two-dimensional image data of a plurality of frames and the position information in the oscillation direction which are sequentially outputted from the scanning conversion means. Therefore, a three-dimensional image with higher geometrical precision in the oscillation direction of the ultrasonic transducer unit can be created.

According to the invention, even if the ultrasonic transducer unit does not perform oscillation scanning at completely constant angular velocity, an actual oscillation scanning angle corresponding to each acquired ultrasonic echo can be given to the three-dimensional processing means. Thus, a three-dimensional image can be structured in a more accurate position spatially.

Further, three-dimensional image processing can be performed based on oscillation angle information equal to or more than the resolution of the minimum oscillation angle.

Further, according to the invention, when a three-dimensional image is created from the two-dimensional images by oscillating the ultrasonic transducer unit, a three-dimensional image with higher geometrical precision in the oscillation direction of the ultrasonic transducer unit can be created.

BRIEF DESCRIPTION OF THE DRAWINGS

FIG. 11 is an explanation drawing showing writing information in a recording region in a frame memory of FIG. 10;

BEST MODE FOR CARRYING OUT THE INVENTION

First Embodiment

Figure 1:
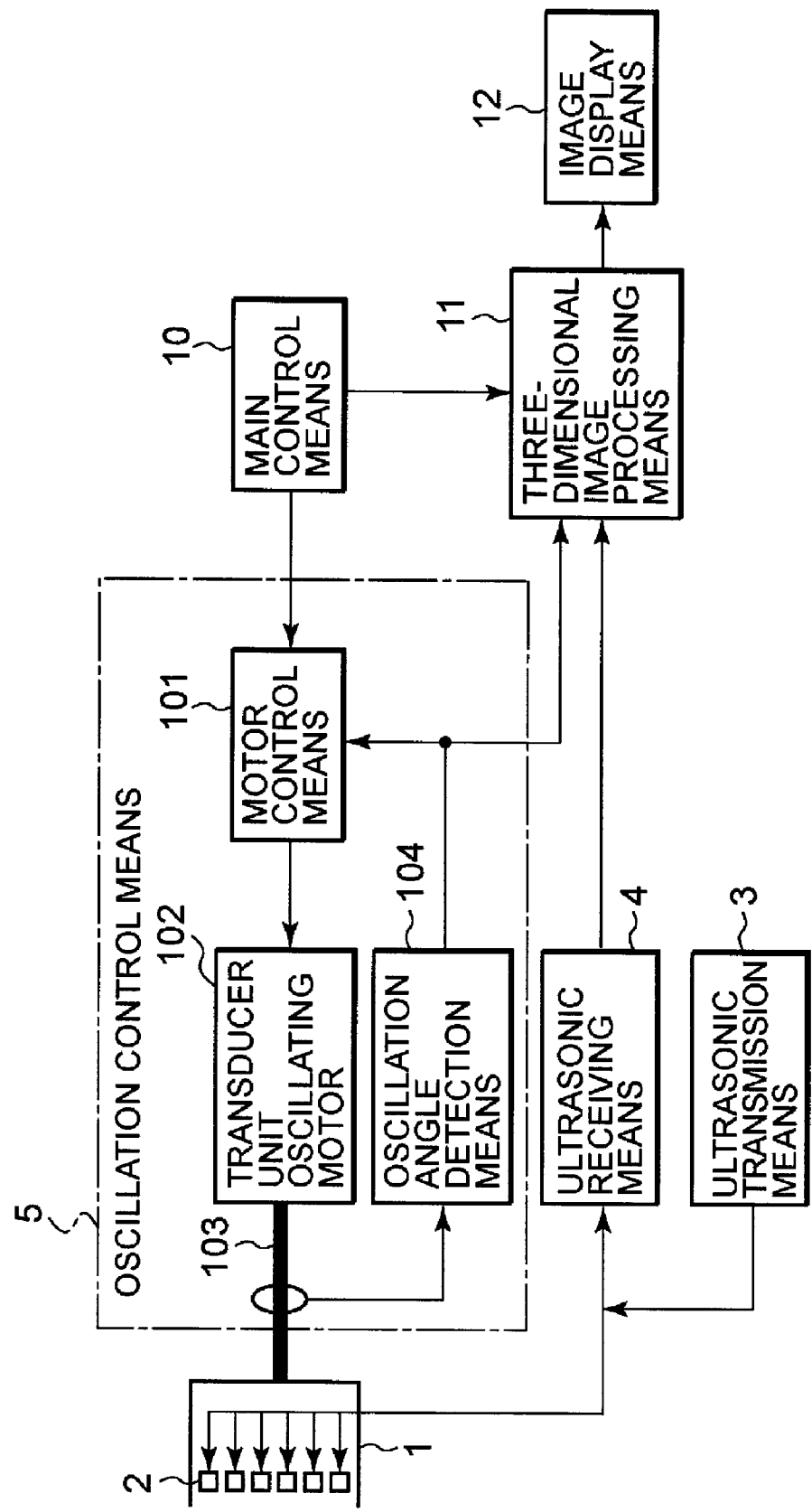
FIG. 1 is a block diagram showing a structure of a first embodiment of an ultrasonographic equipment according to the invention.

FIG. 1 is a block diagram showing a structure of a first embodiment of an ultrasonographic equipment according to the invention. The ultrasonographic equipment includes an ultrasonic transducer unit 1 in which a plurality of ultrasonic transducer elements 2 for transmitting ultrasonic waves into a living body and converting ultrasonic echo from intravital tissues to an electrical signal are arranged in a state of an array. Each ultrasonic transducer element 2 is excited by transmitted pulse supplied from an ultrasonic transmission means 3. Then, the ultrasonic transmission means 3 is controlled to give transmitted pulse in different phases to part or all of the ultrasonic transducer elements 2 arranged in the ultrasonic transducer unit 1 so that a focus is adjusted in a given depth in the living body, that is, transmitted beam is formed in a given depth in the living body.

The ultrasonic waves transmitted into the living body as above is returned as echo every minute from each intravital tissue. For the ultrasonic echo which is converted to an electrical signal by each ultrasonic transducer element 2 of the ultrasonic transducer unit 1, an ultrasonic receiving means 4 performs addition after giving different delay time to each receiving signal from each ultrasonic transducer element 2, so that receiving beam is formed in a given direction. The foregoing transmission beam and the receiving beam form one acoustic scanning line by transmission and receiving. The ultrasonic receiving means 4 creates ultrasonic echo data along the acoustic scanning line, provides demodulation processing for visualizing the ultrasonic echo data, and outputs image data. As above, transmission and receiving are performed so that acoustic scanning lines in different directions are formed while each of the ultrasonic transducer element group used for transmission and receiving is switched from each other sequentially, or while directions of transmission and receiving beam are changed. In result, one main cross section scanned face is formed.

Further, the ultrasonographic equipment includes an oscillation control means 5 composed of a motor control means 101, a transducer unit oscillating motor 102, a rotation transmission means 103, and an oscillation angle detection means 104. Of the foregoing, the transducer unit oscillating motor 102 makes the ultrasonic transducer unit 1 perform oscillation scanning in the direction crossing the foregoing main cross section scanned face. The rotation transmission means 103 transmits rotational movement of the transducer unit oscillating motor 102 to the ultrasonic transducer unit 1. The transducer unit oscillating motor 102 receives oscillation control by the motor control means 101. Information necessary for motor control such as an oscillation angular velocity and an oscillation angle range to the motor control means 101 is received from a main control means 10. By concurrently performing main cross section scanning and oscillation scanning, the ultrasonic receiving means 4 can create ultrasonic echo data corresponding to a cross section of the main cross section scanned face and an oscillation scanned face. In general, the both scanned faces are not scanned independently, but are scanned so that ultrasonic echo data in a specific three-dimensional region in a living f can be uniformly acquired. That is, main cross section scanning and oscillation scanning are performed so that an angle between each main cross section scanned face per one oscillation scanning becomes approximately conformal.

Therefore, it is necessary that the motor control means 101 performs control so that the ultrasonic transducer unit 1 is oscillated at an approximately constant angular velocity during the period of acquiring three-dimensional echo data, while always monitoring at which oscillation scanning angle or at which angular velocity the ultrasonic transducer unit 1 connecting to the transducer unit oscillating motor 102 is operated. Therefore, to obtain an oscillation scanning angle of the ultrasonic transducer unit 1, the ultrasonographic equipment includes the oscillation angle detection means 104 connected to the rotation transmission means 103 which transmits rotational movement of the transducer unit oscillating motor 102 to the ultrasonic transducer unit 1. An arrangement position of the oscillation angle detection means 104 may be the transducer unit oscillating motor 102 side of the rotation transmission means 103, the ultrasonic transducer unit 1 side of the rotation transmission means 103, or an intermediate section between the both sides, as long as information corresponding to the oscillation scanning angle of the ultrasonic transducer unit 1 can be obtained.

Figure 2:
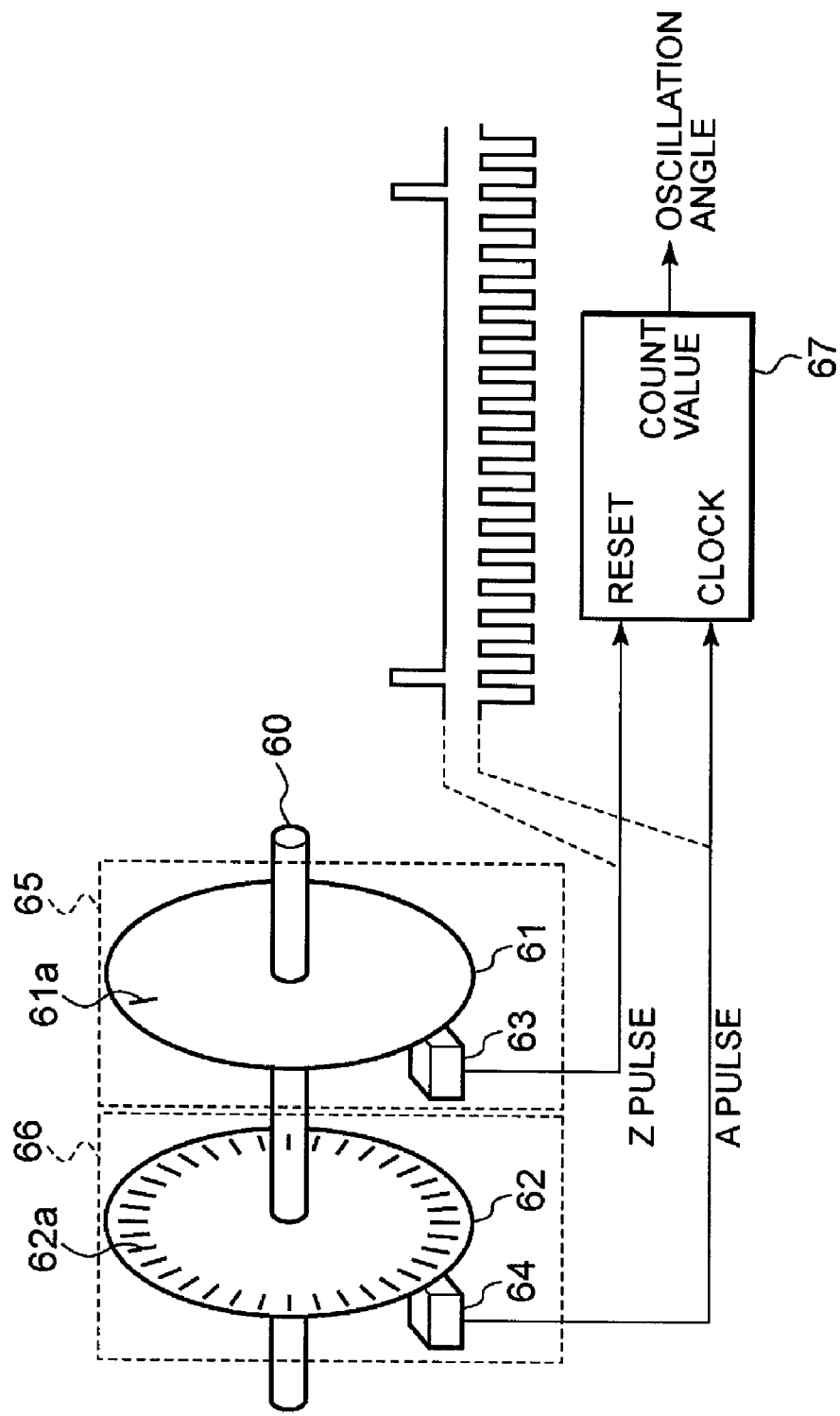
FIG. 2 is an explanation drawing showing an example of an oscillation angle detection means in FIG. 1.

A preferred method of implementing the oscillation angle detection means 104 is a method of attaching a rotary encoder to the rotation transmission means 103. FIG. 2 shows an example thereof. At least two types of rotary encoders are used. In a Z rotary encoder 65 which is one of said at least two encoders, a Z pulse rotor 61 is attached to a rotation shaft 60 so that one pulse (hereinafter referred to as Z pulse) can be outputted at a specific angle of the rotation shaft 60 of the transducer unit oscillating motor 102 which is the rotation transmission means 103. For example, in the case of a magnetic encoder, the z pulse rotor 61 is magnetized to generate one Z pulse per one rotation. A Z pulse sensor 63 detects a magnetized section 61a of the Z pulse rotor 61 to outputs the Z pulse.

Similarly, an A rotary encoder 66 which is the other encoder includes an A pulse rotor 62 which is magnetized (62a in the figure) in a conformal manner to generate several hundred pulse per one rotation of the rotation shaft 60 (hereinafter referred to as A pulse: fixed value) and an A pulse sensor 64. While the foregoing description has been given of the example of the magnetic rotary encoder, the structure of the invention can be applied to an optical rotary encoder and a mechanical rotary encoder. The A pulse and the Z pulse from the rotary encoders 65, 66 are transmitted to an encoder pulse counter 67.

The encoder pulse counter 67 is reset by the Z pulse from the Z rotary encoder 65. The encoder pulse counter 67 counts up or counts down a value based on the A pulse from the rotary encoder 66. A count value as a result of counting corresponds to a rotation shaft angle of the transducer unit oscillating motor 102, that is, an oscillation scanning angle of the ultrasonic transducer unit 1. The motor control means 101 can learn a current oscillation scanning angle of the ultrasonic transducer unit 1 from the count value of the oscillation angle detection means 104 as above. Therefore, the motor control means 101 controls the transducer unit oscillating motor 102 to move the ultrasonic transducer unit 1 at a given next oscillation scanning angle. When a current oscillation scanning angular velocity is used for oscillation control, the oscillation scanning angular velocity can be obtained by a time difference of oscillation scanning angles.

Image data of the ultrasonic echo in the specific three-dimensional region in the living body which is acquired by concurrently performing main cross section scanning and oscillation scanning is transmitted to a three-dimensional image processing means 11. The three-dimensional image processing means 11 performs three-dimensional image processing so that a structure in the specific three-dimensional region in the living body on an image display means 12 as if the image is a three-dimensional image which is observed from a virtual view point. Otherwise, the three-dimensional image processing means 11 performs three-dimensional image processing so that a cross section obtained by cutting the three-dimensional structure in a given plane is displayed. To implement the three-dimensional image processing, it is necessary that to which direction component in the three-dimensional space the acquired ultrasonic echo data of each acoustic scanning line belongs is known. The three-dimensional image processing means 11 in the invention acquires a scanning direction angle in the main cross section scanned face from arrangement of the ultrasonic transducer element 2 composing the ultrasonic transducer unit 1 and a direction of transmission and receiving beam. Further, the three-dimensional image processing means 11 acquires an oscillation angle of the oscillation scanned face from oscillation angle information from the oscillation angle detection means 104.

Figure 3A:
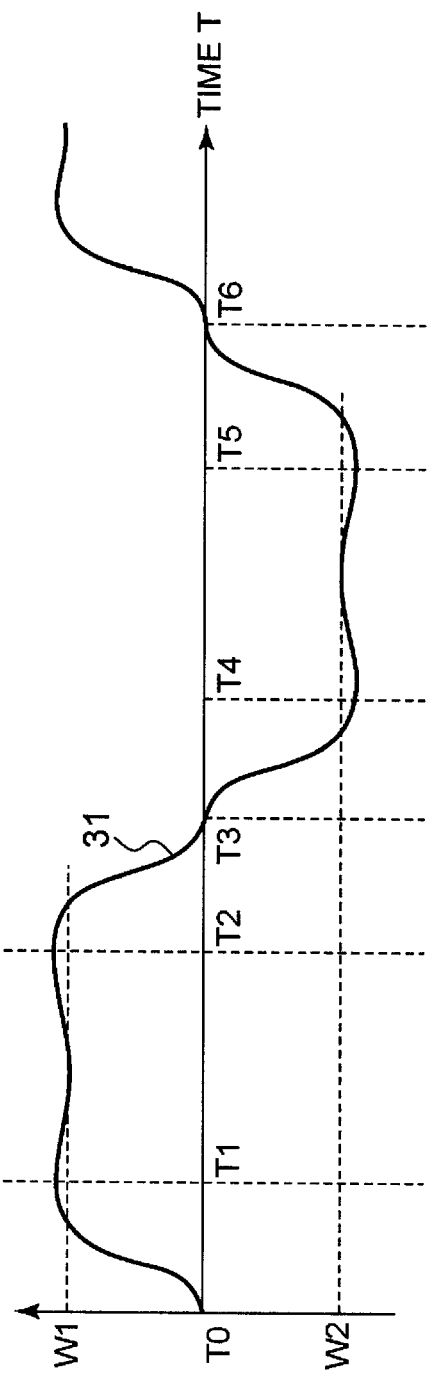
FIG. 3A is an explanation drawing showing a profile of actual oscillation angular velocity of an ultrasonic transducer element in mechanical scanning method.
Figure 3B:
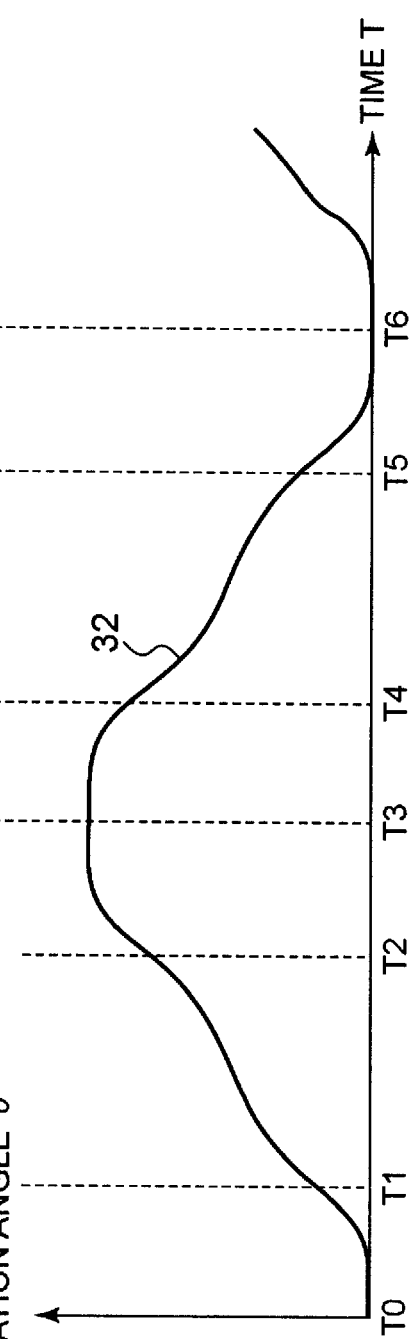
FIG. 3B is an explanation drawing showing a profile of actual oscillation angle of the ultrasonic transducer element in the mechanical scanning method.
Figure 4:
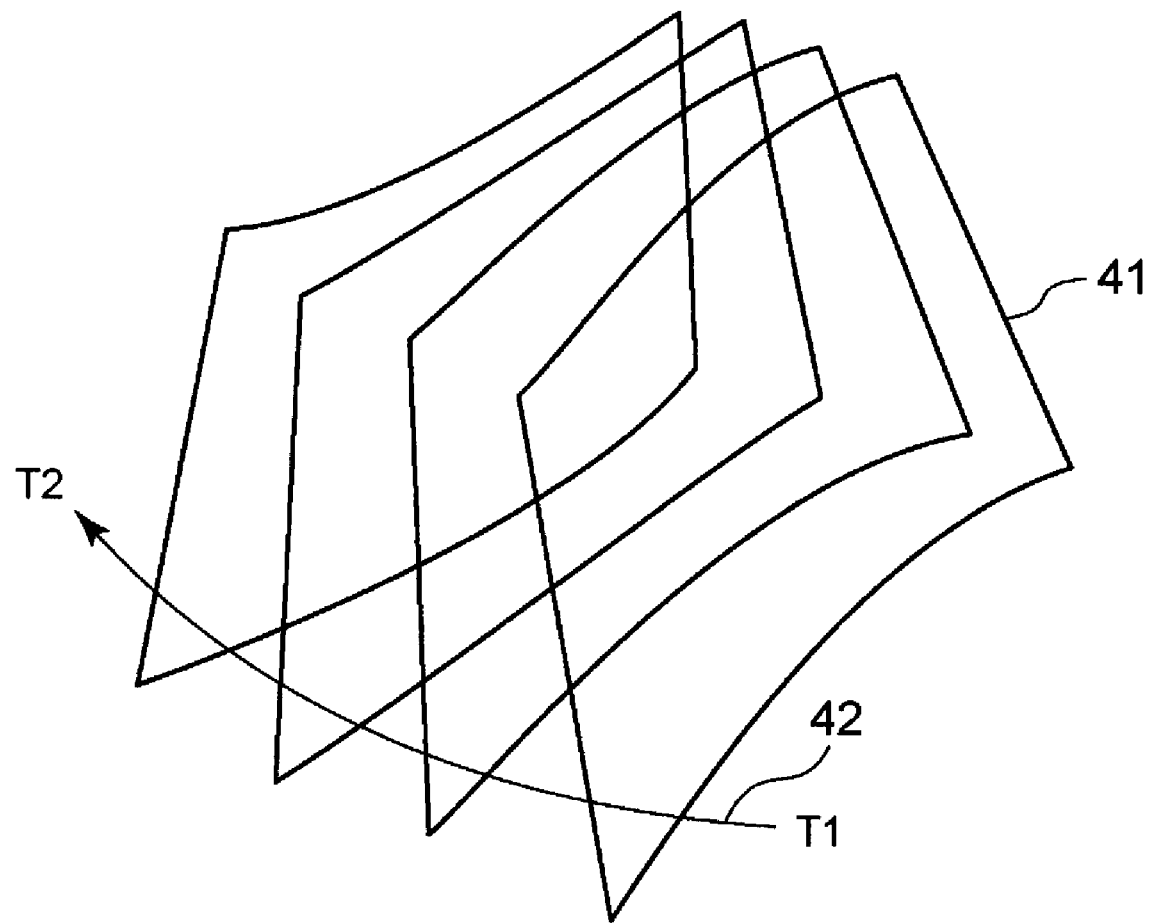
FIG. 4 is an explanation drawing showing a shape of a main cross section scanned face before correction in the invention.

In general, in the three-dimensional display ultrasonographic equipment using mechanical scanning method as oscillation scanning, even when the transducer unit oscillating motor 102 is controlled by the motor control means highly precisely, it is not possible to perform complete oscillation constant angular velocity movement. An actual transducer unit oscillation angular velocity W and a resultant oscillation angle θ at certain time T result in profiles 31, 32 as shown in FIGS. 3A and 3B respectively. That is, even during outward period T1 to T2 and homeward period T4 to T5 when relatively stable constant angular velocity scanning is possibly performed, the oscillation angular velocity profile 31 in relation to time moves with certain variations in the vicinity of angular velocities W1, W2, and the oscillation angle profile 32 in relation to time does not result in a straight line during the same periods. Therefore, for example, each actual main cross section scanned face obtained during period 42 between time T1 and time T2 (refer to FIG. 4) becomes a group of main cross section scanned faces 41 which are curved faces as shown in FIG. 4.

Here, in the ultrasonographic equipment according to the invention with the structure shown in FIG. 1, even if oscillation scanning of the ultrasonic transducer unit 1 is not performed at a completely constant angular velocity, that is, even if each main cross section scanned face is not a plane, the oscillation angle detection means 104 can notify the actual oscillation angle θ of the ultrasonic transducer unit 1 at the time when each ultrasonic echo is acquired to the three-dimensional image processing means 11. Therefore, the three-dimensional image based on the actual oscillation angle can be structured. In result, the three-dimensional image can be structured in more accurate position spatially.

Second Embodiment

Figure 5:
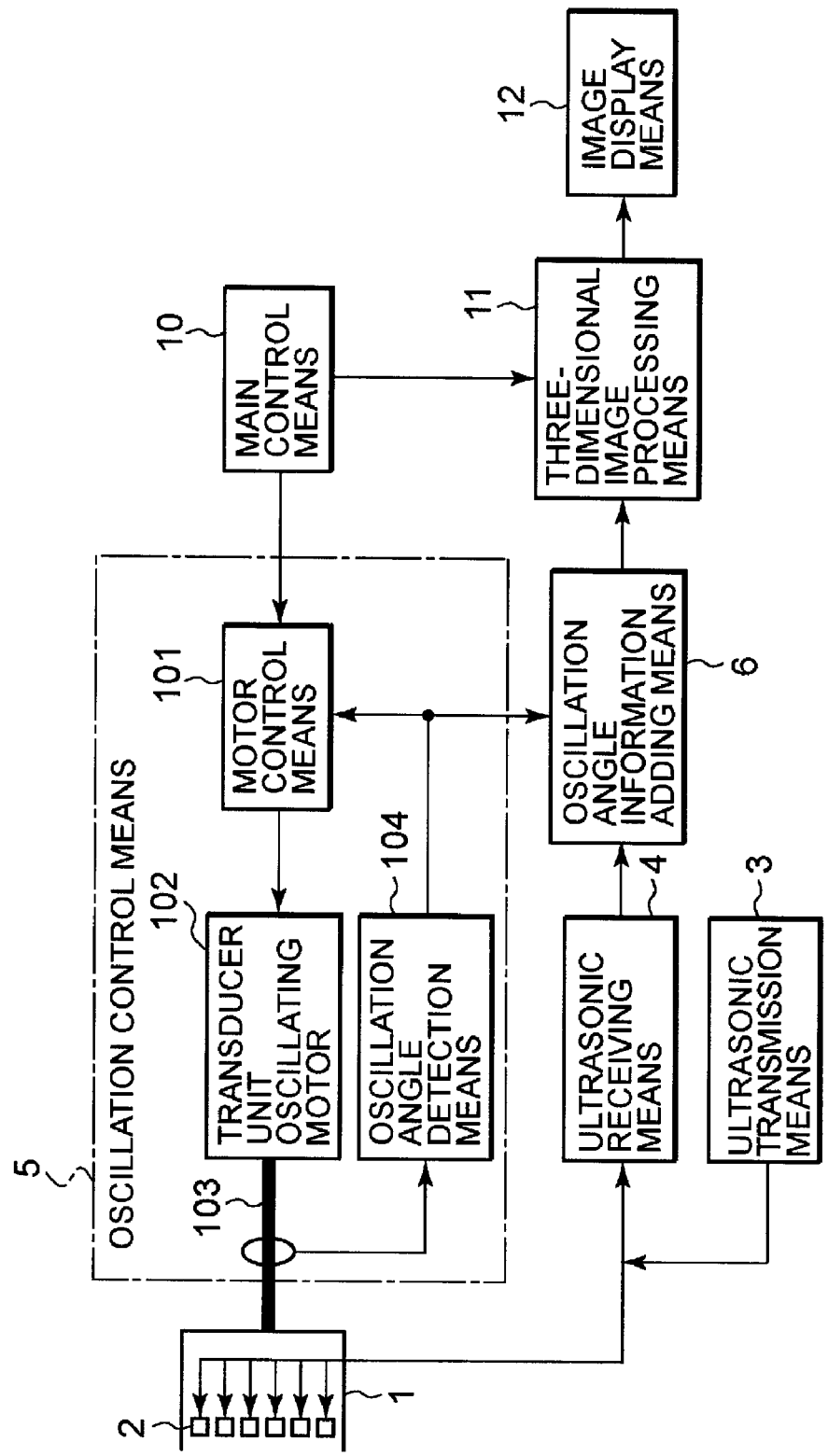
FIG. 5 is a block diagram showing a structure of a second embodiment of the ultrasonographic equipment according to the invention.

Next, a description will be given of a second embodiment of the invention. FIG. 5 is a block diagram showing a structure of the second embodiment of the ultrasonographic equipment according to the invention. In the foregoing first embodiment, image data from the ultrasonic receiving means 4 and oscillation angle information from the oscillation angle detection means 104 are inputted to the three-dimensional image processing means 11. However, in line with the spirit of the invention, it is enough that a piece of oscillation angle information exists for a piece of image data of one acoustic scanning line for the purpose of structuring a three-dimensional image. That is, compared to a data amount per unit time of image data, a data amount per unit time of oscillation angle information is significantly small. Meanwhile, in general, image data from the ultrasonic receiving means 4 is not always effective. In advance of acquiring ultrasonic echo, blanking time to secure parameter setting time for each circuit block is generated. That is, image data arrays are to be inputted to the three-dimensional image processing means 11 intermittently.

In the second embodiment of the invention, preceding the three-dimensional image processing means 11, an oscillation angle information adding means 6 for selecting image data from the ultrasonic receiving means 4 and oscillation angle information from the oscillation angle detection means 104 is provided. Thus image data including the blanking time added with the oscillation angle information is inputted to the three-dimensional image processing means 11.

Figure 6:
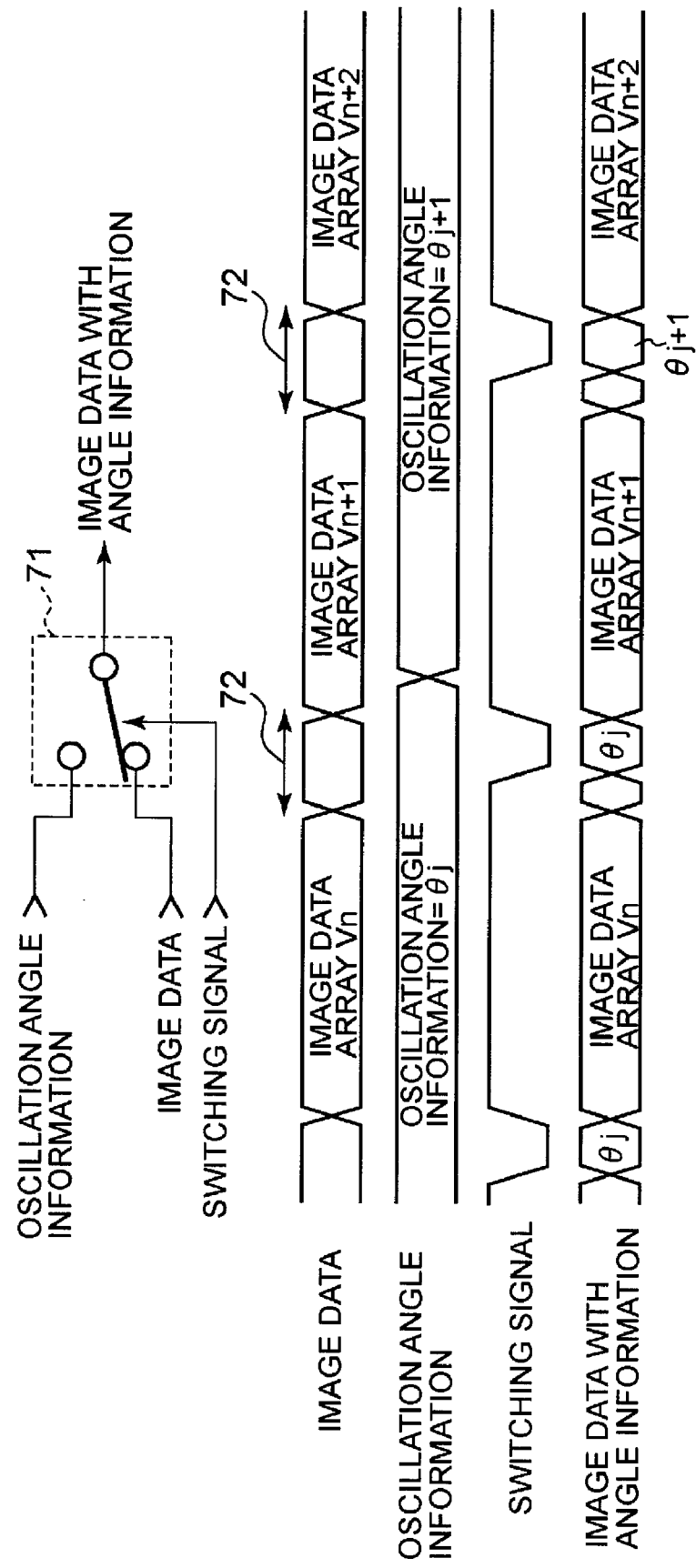
FIG. 6 is an explanation drawing showing a structural example of an oscillation angle information adding means in FIG. 5 and image data with angle information.

A description will be given of a structural example of the oscillation angle information adding means 6 and data by using FIG. 6. In the oscillation angle information adding means 6 of this embodiment, as a method to add oscillation angle information to image data, a switch 71 for switching image data from the ultrasonic receiving means 4 and oscillation angle information from the oscillation angle detection means 104 is provided. Each image data array corresponding to one acoustic scanning line such as Vn, Vn+1, Vn+2 and so on intermittently associated with blanking time 72 is inputted from the ultrasonic receiving means 4 to the oscillation angle information adding means 6. The switch 71 captures the blanking time 72 by determining the blanking time 72 from the image data array or inputting the blanking time 72 from outside. The switch 71 selects oscillation angle information θj, θj+1 and so on during part of the blanking time 72 (from the front side, from the rear side, or from a position apart from the front side under certain conditions) or during the whole time of the blanking time 72. The switch 71 selects the image data arrays Vn, Vn+1, Vn+2 and so on during time other than the foregoing. Therefore, in the output of the switch 71, image data arrays with angle information in which the oscillation angle information θj, θj+1 and so on are added to the blanking time 72 of the acoustic scanning line image data arrays Vn, Vn+1, Vn+2 and so on are shown.

As above, the image data arrays with angle information are inputted to the three-dimensional image processing means 11. Therefore, in three-dimensional image processing, the oscillation angle information θj, θj+1 and so on for the image data arrays Vn, Vn+1, Vn+2 and so on of each acoustic scanning line can be acquired from the image data arrays with angle information. In result, a three-dimensional image based on the actual oscillation scanning angle θ can be structured, and the three-dimensional image can be structured in a more accurate position spatially. In addition, interfaces to the three-dimensional image processing means 11 can be simplified, and therefore a circuit physical quantity and the cost can be reduced.

Third Embodiment

Figure 7:
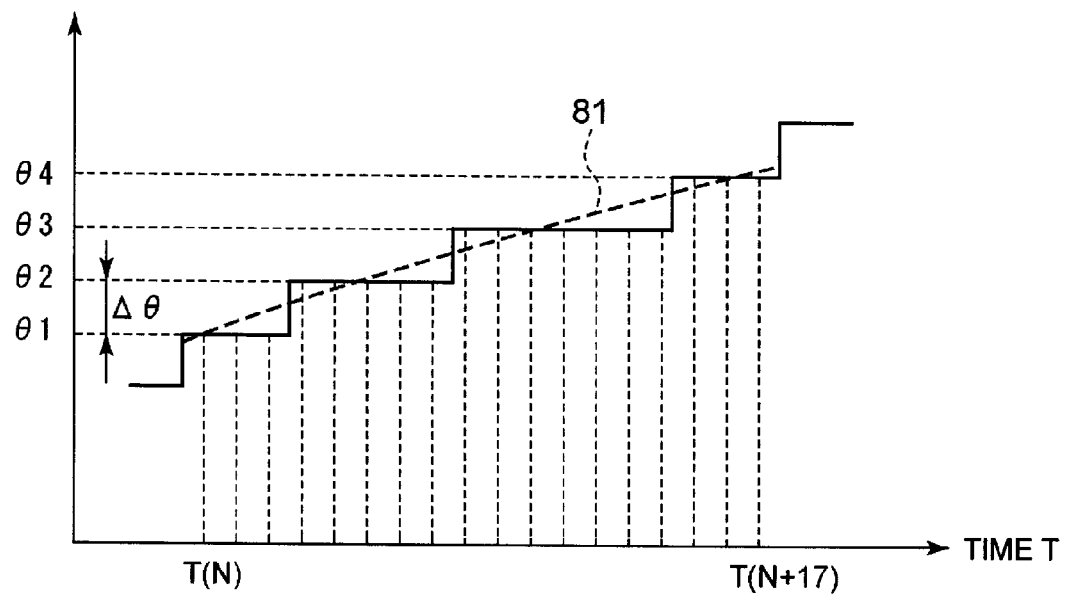
FIG. 7 is an explanation drawing showing smoothing processing of angle information in a third embodiment of the ultrasonographic equipment according to the invention.

Next, a description will be given of a third embodiment of the invention. As described above, the oscillation angle information corresponding to the actual oscillation scanning angle θ of the ultrasonic transducer unit 1 is obtained by the oscillation angle detection means 104. In the rotary encoder method generally used, an actual oscillation scanning angle of the ultrasonic transducer unit 1 corresponding to a generation unit of the A pulse of the A rotary encoder 66 becomes the minimum resolution of oscillation angle detection. An example of performing certain main cross section scanning over time T(N) to T(N+17) is shown in full line in FIG. 7. An actual oscillation angle of an acoustic scanning line acquired during the time T(N) to T(N+2) is θ1. An actual oscillation angle of an acoustic scanning line acquired during the time T(N+3) to T(N+7) is θ2. The same is applied up to the time T(N+17). Here, the minimum resolution of oscillation angle detection is expressed as Δθ=θ2−θ1.

Figure 8:
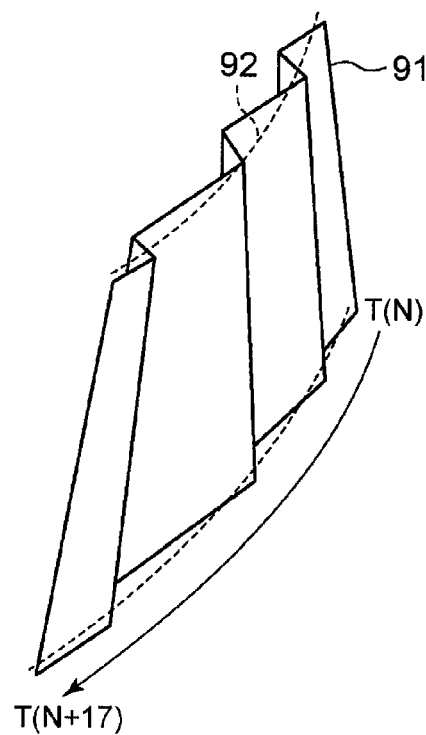
FIG. 8 is an explanation drawing showing smoothing processing of an image in the third embodiment of the ultrasonographic equipment according to the invention.

As shown in full line in FIG. 8, a main cross section scanned face 91 which is structured by straightly using image data and the actual oscillation angles θ1 to θ4 of an acoustic scanning line acquired at each time is in a state of steps corresponding to the size of Δθ. Therefore, Δθ is desirably small as long as possible. To attain the small Δθ, there are methods such as increasing the number of pulse generation per one rotation of the A pulse rotor 62, and adding a separate rotary encoder to the rotation shaft 60. However, to realize such a method, problems of increasing the cost and increasing the physical quantity occur.

The three-dimensional image processing means 11 structuring the ultrasonographic equipment of the third embodiment of the invention has a function of smoothing the actual oscillation scanning angles θ1, θ2, θ3 and so on of the ultrasonic transducer unit 1 added to each acoustic scanning line. The three-dimensional image processing means 11 structures a three-dimensional image by using an oscillation angle smoothing result 81 shown in dotted line in FIG. 7. As a smoothing method, linear interpolation, spline interpolation, Newton interpolation or the like can be used as appropriate. As above, the three-dimensional image processing means 11 can structure a three-dimensional image by newly referencing the obtained oscillation angle smoothing result 81 as an oscillation angle of each ultrasonic echo. Therefore, a main cross section scanned face 92 after smoothing as shown in dotted line in FIG. 8 can be structured, and more natural three-dimensional image can be structured.

Fourth Embodiment

Figure 9:
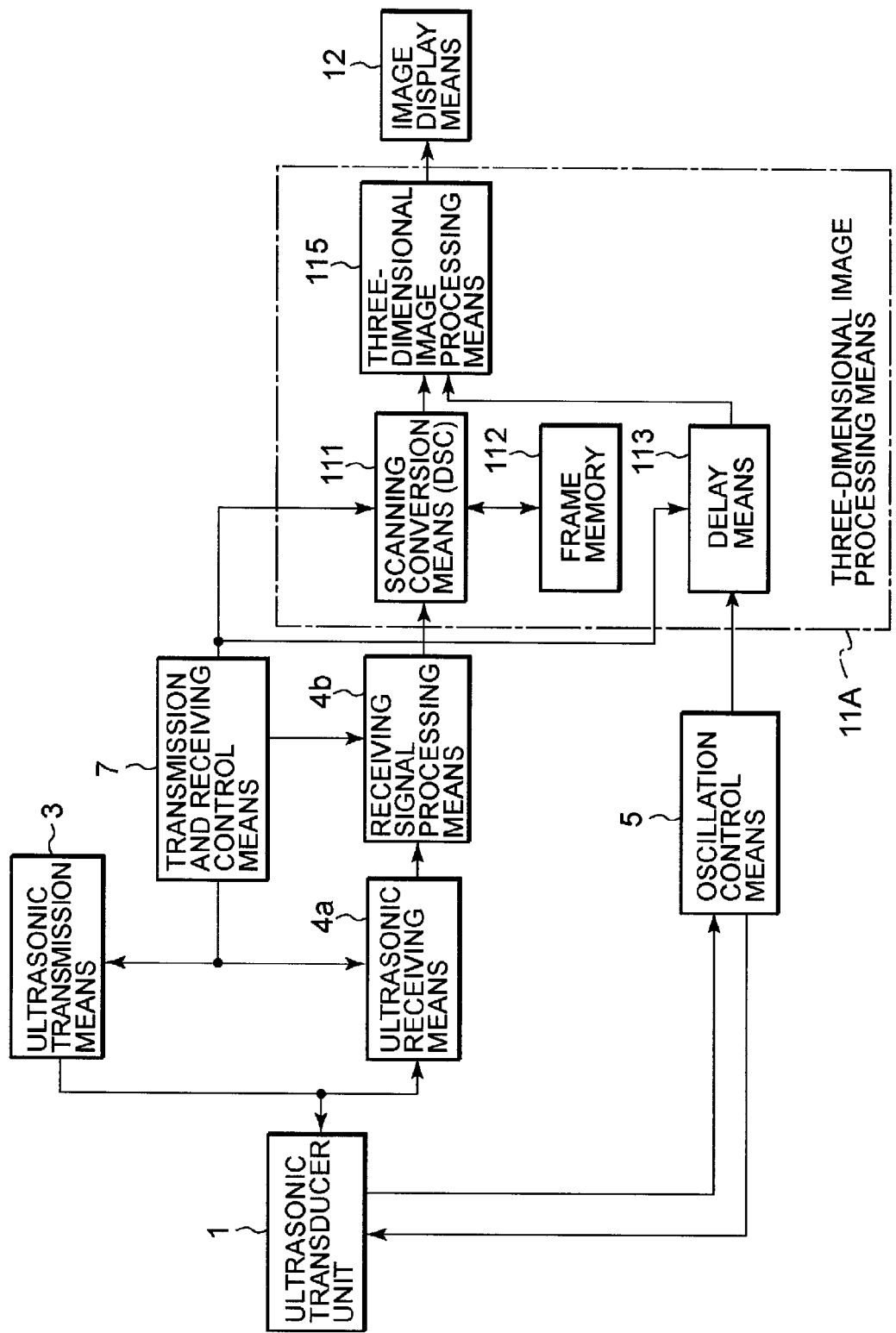
FIG. 9 is a block diagram showing a structure of a fourth embodiment of the ultrasonographic equipment according to the invention.

FIG. 9 is a block diagram showing a structure of a fourth embodiment of the ultrasonographic equipment according to the invention. In FIG. 9, a transmission and receiving control means 7 which is not shown in FIG. 1 showing the first embodiment is added, the ultrasonic receiving means 4 in FIG. 1 is shown by being divided into an ultrasonic receiving means 4a and a receiving signal processing means 4b according to each function, and details of a three-dimensional image processing means 11A corresponding to the three-dimensional image processing means 11 of FIG. 1 are shown. The three-dimensional image processing means 11A includes a scanning conversion means 111, a frame memory 112, a delay means 113, and a three-dimensional image processing means 115.

Next, a description will be given of operations of the forth embodiment. Based on control by the transmission and receiving control means 7, the ultrasonic transducer unit 1 in an unshown ultrasonic probe transmits an ultrasonic signal from the ultrasonic transmission means 3, and the ultrasonic receiving means 4a receives a reflection signal thereof. Based on control of the transmission and receiving control means 7, the ultrasonic receiving means 4a creates ultrasonic echo data along an acoustic scanning line and adds the created ultrasonic echo data to the receiving signal processing means 4b. The receiving signal processing means 4b provides demodulation processing to visualize the ultrasonic echo data, and outputs image data. The image data outputted from the receiving signal processing means 4b is sent to the three-dimensional image processing means 11A.

The image data sent to the three-dimensional processing means 11A is inputted to the scanning conversion means (DSC) 111. The scanning conversion means 111 records echo data for every one frame in the frame memory 112, creates a two-dimensional image of the X-Y plane, reads out the created two-dimensional image, and adds the read image to the three-dimensional image processing means 115. The echo data is a digital signal, and is created by an A/D converter (not shown) for A/D converting an analog signal outputted from the ultrasonic transducer unit 1. The A/D converter can be provided in a given position between the ultrasonic transducer unit 1 and the scanning conversion means 111.

Further, in the unshown ultrasonic probe which contains the ultrasonic transducer unit 1, to oscillate the ultrasonic transducer unit 1 in the Z direction, the transducer unit oscillating motor 102 and the oscillation angle detection means 104 which are shown in FIG. 1 are provided. The transducer unit oscillating motor 102 and the oscillation angle detection means 104 compose the oscillation control means 5. As described above, the oscillation angle detection means 104 includes the rotary encoders 65, 66 (refer to FIG. 2) and the encoder pulse counter 67 for counting the pulse thereof. Oscillation angle information expressing a current oscillation scanning angle of the ultrasonic transducer unit 1 is sent to the delay means 113. The delay means 113 delays the oscillation angle information by the processing portion of the scanning conversion means 111 based on ultrasonic transmission and receiving timing of the transmission and receiving control means 7, and sends the delayed oscillation angle information to the three-dimensional image processing means 115. The three-dimensional image processing means 115 creates a three-dimensional image based on the oscillation angle information delayed by the delay means 113 from the two-dimensional images of the X-Y plane of the plurality of frames from the scanning conversion means 111, and sends the three-dimensional image to the image display means 12.

By the foregoing structure, timing of the two-dimensional image inputted to the three-dimensional image processing means 115 and an oscillation angle in the Z direction of the ultrasonic transducer unit 1 are synchronized. Therefore, a three-dimensional image with higher geometric precision in the oscillation direction can be created.

Fifth Embodiment

Figure 10:
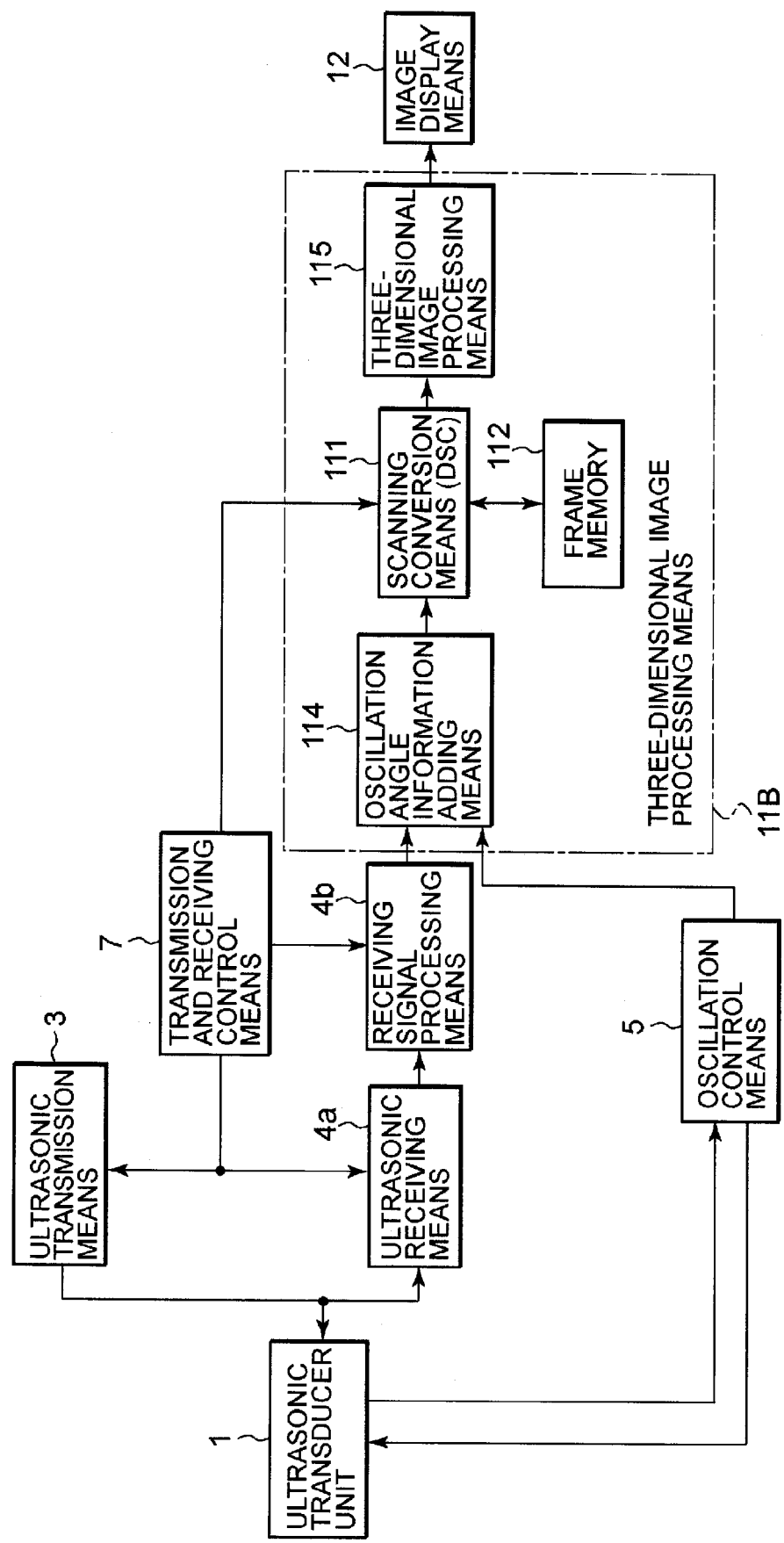
FIG. 10 is a block diagram showing a structure of a fifth embodiment of the ultrasonographic equipment according to the invention.
Figure 12:
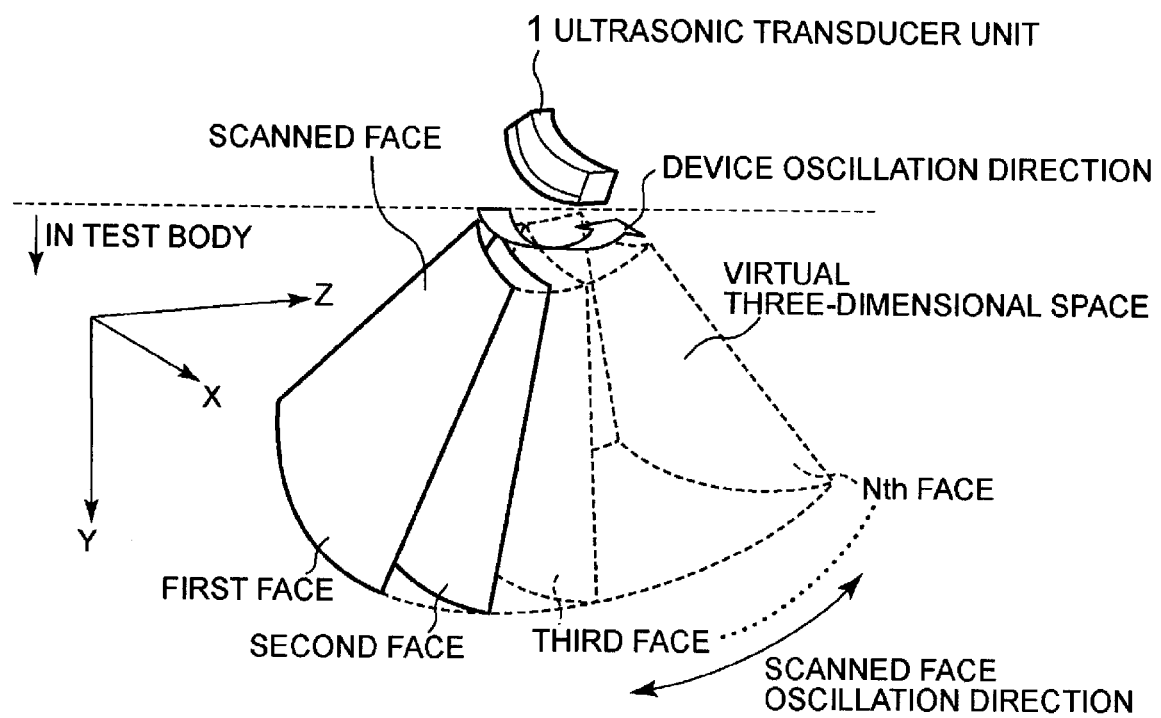
FIG. 12 is an explanation drawing showing an oscillation state of a general ultrasonic transducer unit.
Figure 13A:
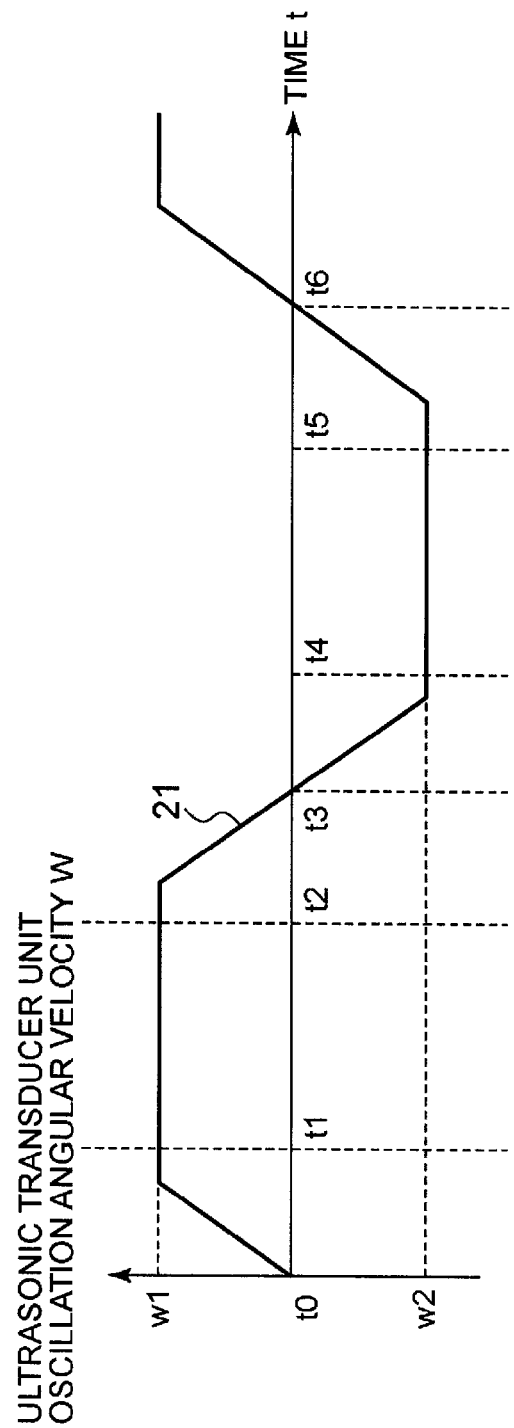
FIG. 13A is an explanation drawing showing a profile of ideal oscillation angular velocity in relation to time of an ultrasonic transducer unit.
Figure 13B:
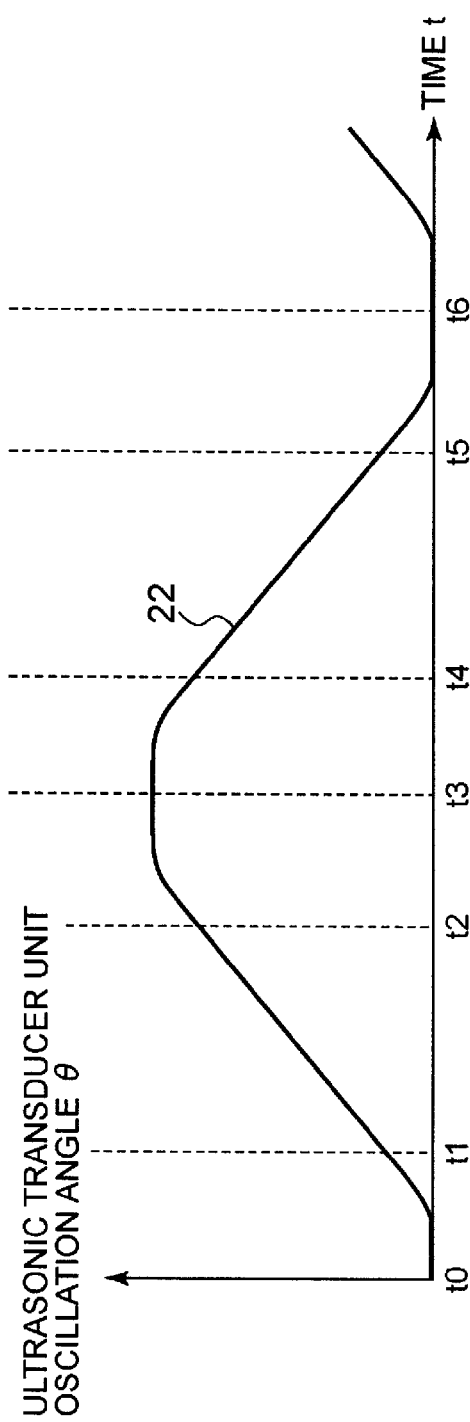
FIG. 13B is an explanation drawing showing a profile of ideal oscillation angle in relation to time of the ultrasonic transducer unit.
Figure 14:
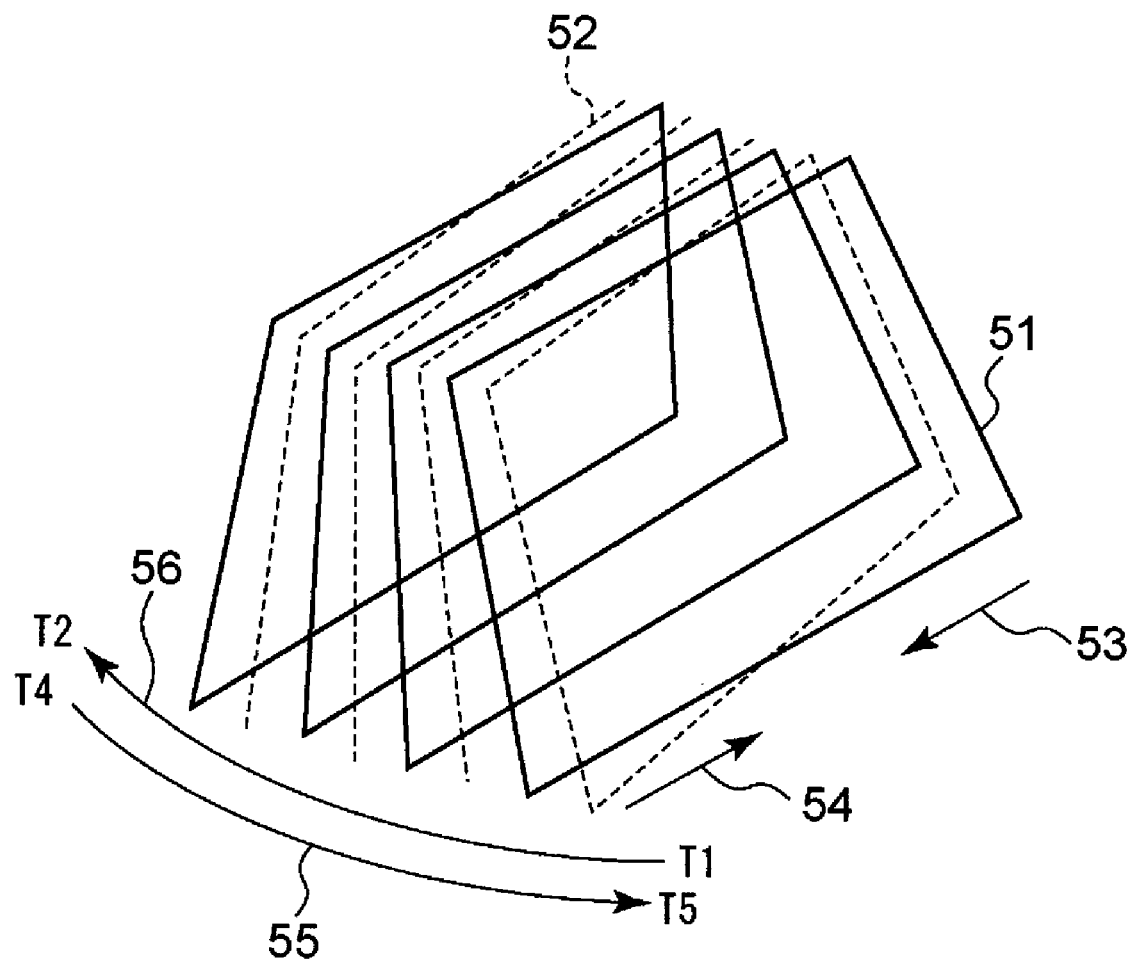
FIG. 14 is an explanation drawing showing a shape of a main cross section scanned face of a related art.

FIG. 10 is a block diagram showing a structure of a fifth embodiment of the ultrasonographic equipment according to the invention. FIG. 11 is an explanation drawing showing writing information in a recording region in a frame memory of FIG. 10. Of the components shown in FIG. 10, the same components as those in FIG. 9 showing the forth embodiment are affixed with the same referential characters, and explanation thereof will be omitted. This embodiment differs in that a three-dimensional image processing means 11B is provided instead of the three-dimensional image processing means 11A in FIG. 9. The three-dimensional image processing means 11B includes an oscillation angle information adding means 114 structured identically to the oscillation angle information adding means 6 in FIG. 5 showing the second embodiment. In addition, the three-dimensional image processing means 11B includes the scanning conversion means (DSC) 111, the frame memory 112, and the three-dimensional image processing means 115 explained with reference to FIG. 9.

Next, for the operations of the fifth embodiment, a description will be given of sections with structures different from those of the forth embodiment. As described in the second embodiment in detail, the oscillation angle information adding means 114 receives image data from the receiving signal processing means 4b and oscillation angle information from the oscillation angle detection means 104 (refer to FIG. 5) composing the oscillation control means 5. Image data with blanking time added with the oscillation angle information is inputted to the scanning conversion means (DSC) 111. As shown in FIG. 11, the scanning conversion means (DSC) 111 records receiving data for every one frame in the recording region 112a in the frame memory 112 to create a two-dimensional image of the X-Y plane, records oscillation angle information corresponding to a position of an acoustic line of each ultrasonic transducer element 2 of the ultrasonic transducer unit 1 as oscillation angle information from the oscillation angle detection means 104, reads out the two-dimensional image and the oscillation angle information, and outputs the same to the three-dimensional image processing means 115.

The oscillation angle information may be written for every acoustic line of each ultrasonic transducer element of the ultrasonic transducer unit 1 as shown in FIG. 11. Otherwise, only an oscillation angle representing one frame may be written. For example, only an angle of the front end, the center, or the rear end in one frame may be written. Further, such a representative value may be recorded as the same value in a recording region of angle information in the same frame.

The three-dimensional image processing means 115 develops the two-dimensional images of the X-Y plane of a plurality of frames from the scanning conversion means 111 to a three-dimensional image based on the oscillation angle information. Then, the three-dimensional image processing means 115 sends the three-dimensional image data to the image display means 12. By such a structure, a three-dimensional image with higher geometrical precision in the oscillation direction can be created.

INDUSTRIAL APPLICABILITY

As described above, the ultrasonographic equipment according to the invention can provide an actual oscillation scanning angle corresponding to each acquired ultrasonic echo to the three-dimensional image processing means, even when the ultrasonic transducer unit does not perform oscillation scanning at a completely constant angular velocity. Further, the ultrasonographic equipment can structure a three-dimensional image in a more accurate position spatially. Furthermore, the ultrasonographic equipment can perform three-dimensional image processing based on oscillation angle information of the minimum oscillation angle resolution or more. The invention is useful for an ultrasonographic equipment or the like in which intravital echo data is three-dimensionally acquired, the data is converted to image data from a virtual viewpoint, and the image data is displayed.

The invention claimed is:
1. An ultrasonographic equipment comprising:
   an ultrasonic transducer unit in which ultrasonic transducer elements for scanning an ultrasonic beam are arranged in a state of an array;
   a transducer unit oscillating motor for making the ultrasonic transducer unit perform oscillation scanning in the direction crossing the scanning direction of the ultrasonic beam;
   an oscillation angle detector configured to detect an oscillation angle of the ultrasonic transducer unit and generating oscillation angle information;
   an ultrasonic transmitter configured to excite the ultrasonic transducer elements to form the ultrasonic beam;
   an ultrasonic receiver configured to form the ultrasonic beam from an ultrasonic echo received by the ultrasonic transducer elements and converting the ultrasonic beam to an image data array;
   a three-dimensional image processor configured to receive data streams comprising intermittent image data arrays with corresponding oscillation angle information inserted at blanking times between the image data arrays, the three-dimensional image processor further configured to form a three-dimensional image based on the data streams; and
   an image display configured to display the three-dimensional image.
2. The ultrasonographic equipment according to claim 1, wherein the three-dimensional image processor forms a three-dimensional image based on angle information obtained by interpolating the oscillation angle information detected by the oscillation angle detector.

3. An ultrasonographic equipment comprising:
an ultrasonic transducer unit in which ultrasonic transducer elements for scanning an ultrasonic beam are arranged in a state of an array;
a transducer unit oscillating motor for making the ultrasonic transducer unit perform oscillation scanning in the direction crossing the scanning direction of the ultrasonic beam;
an oscillation angle detector configured to detect an oscillation angle of the ultrasonic transducer unit and generating oscillation angle information;
an ultrasonic transmitter configured to excite the ultrasonic transducer elements to form the ultrasonic beam;
an ultrasonic receiver configured to form the ultrasonic beam from an ultrasonic echo received by the ultrasonic transducer elements and converting the ultrasonic beam to an image data array;
an oscillation angle information adder configured to add the oscillation angle information generated by the oscillation angle detector into the image data array outputted from the ultrasonic receiver to form data streams, wherein the data streams comprise intermittent image data arrays with blanking times between the image data arrays, and the oscillation angle information is data inserted at the blanking times between the image data arrays by the oscillation angle information adder, such that the data streams comprise the intermittent image data arrays with corresponding oscillation angle information inserted at the blanking times between the image data arrays;
a three-dimensional image processor configured to receive the data streams and to form a three-dimensional image based on the image data arrays and the corresponding oscillation angle information outputted from the oscillation angle information adder; and
an image display configured to display the three-dimensional image.

4. The ultrasonographic equipment according to claim 3, wherein the three-dimensional image processor forms a three-dimensional image based on angle information obtained by interpolating the oscillation angle information detected by the oscillation angle detector.

5. An ultrasonographic equipment comprising:
an ultrasonic transducer unit which two-dimensionally scans a fault plane of a test body, and is driven to be oscillated in the direction orthogonal to a scanned face of the two-dimensional scanning;
a scanning converter configured to receive data streams comprising intermittent image data arrays with corresponding oscillation angle information inserted at blanking times between the image data arrays, the scanning converter further configured to record a receiving signal obtained by the two-dimensional scanning by the ultrasonic transducer unit in a frame memory to create two-dimensional image data, write position information in the oscillation direction of the ultrasonic transducer unit in the frame memory, read out the two-dimensional image data and the position information, and output the two-dimensional image data and the position information; and
a three-dimensional image processor configured to create a three-dimensional image from the two-dimensional image data of a plurality of frames and the position information in the oscillation direction which are sequentially outputted from the scanning converter.

* * * * *